United States Patent [19]
Engel et al.

[11] Patent Number: 5,663,145
[45] Date of Patent: Sep. 2, 1997

[54] PRODUCTS FOR ADMINISTERING AN INITIAL HIGH DOSE OF CETRORELIX AND PRODUCING A COMBINATION PACKAGE FOR USE WHEN TREATING DISEASES

[75] Inventors: Jurgen Engel, Alzenau; Peter Hilgard; Thomas Reissmann, both of Frankfurt, all of Germany

[73] Assignee: ASTA Medica Aktiengesellschaft, Dresden, Germany

[21] Appl. No.: 354,838

[22] Filed: Dec. 8, 1994

[30] Foreign Application Priority Data

Dec. 9, 1993 [DE] Germany ............ 43 42 091.5

[51] Int. Cl.$^6$ ................................. A61K 38/09
[52] U.S. Cl. ................................. 514/15; 514/800
[58] Field of Search ............ 206/532, 534.1, 206/539; 514/15.8; 530/313; 930/130

[56] References Cited

U.S. PATENT DOCUMENTS

| | | | |
|---|---|---|---|
| 4,305,502 | 12/1981 | Gregory et al. | 206/532 |
| 4,569,927 | 2/1986 | Rivier et al. | 514/15 |
| 4,817,819 | 4/1989 | Kelly et al. | 206/539 |
| 5,046,618 | 9/1991 | Wood | 205/532 |
| 5,064,813 | 11/1991 | Labrie | 514/15 |
| 5,116,818 | 5/1992 | Hodgen et al. | 514/15 |
| 5,171,835 | 12/1992 | Janaky et al. | 530/313 |
| 5,480,868 | 1/1996 | Kamei et al. | 514/15 |

FOREIGN PATENT DOCUMENTS

| | | | |
|---|---|---|---|
| 81285 | 12/1988 | Austria . | |
| 0002495 | 6/1979 | European Pat. Off. . | |
| 63290 | 10/1982 | European Pat. Off. | 206/532 |
| 0089548 | 9/1983 | European Pat. Off. . | |
| 0132102 | 1/1985 | European Pat. Off. . | |
| 0171550 | 2/1986 | European Pat. Off. . | |
| 0237159 | 9/1987 | European Pat. Off. . | |
| 0268066 | 5/1988 | European Pat. Off. . | |
| 0294493 | 12/1988 | European Pat. Off. . | |
| 0299402 | 1/1989 | European Pat. Off. . | |
| 0315414 | 5/1989 | European Pat. Off. . | |
| 0442671 | 8/1991 | European Pat. Off. . | |
| 0569096 | 11/1993 | European Pat. Off. . | |
| 2241740 | 3/1973 | Germany . | |
| 2335265 | 1/1975 | Germany . | |
| 2729068 | 1/1979 | Germany . | |
| 2840461 | 3/1979 | Germany . | |
| 2834226 | 2/1980 | Germany . | |
| 2907452 | 11/1988 | Germany . | |
| 3823590 | 1/1989 | Germany . | |
| 1554911 | 4/1990 | U.S.S.R. . | |
| 1204580 | 9/1970 | United Kingdom . | |
| WO9003182 | 4/1990 | WIPO . | |
| WO9011070 | 10/1990 | WIPO . | |

OTHER PUBLICATIONS

J. Clin. Endo. Metab., vol. 75, No. 2, issued 1992, Behre et al, "Effective Suppression of Luteinizing Hormone . . . ", pp. 393–398.
PNAS USA, vol. 87, issued Sep. 1990, Bokser et al, "Prolonged inhibition of luteinizing hormone . . . ", pp. 7100–7104.
Search Report dated Feb. 7, 1995.
Austria–Codex, Fachinformation 1993/94, A–F, p. 808.
Austria–Codex, Fachinformation 1993/94, G–Q, pp. 2144–2147.
Austria–Codex, Fachinformation 1993/94, R–Z, pp. 3530, 3531, 3544–3549.
Proceedings Of The National Academy of Sciences of the United States of America, Jan. 1, 1991, vol. 88, No. 1, entitled "Inhibition . . . SB–75", pp. 844–848.
Decapeptyl Controlled Release in prostate cancer, pp. 6–26 (not dated).
Released, Asta Pharma, Report dated Sep. 19, 1990, Project No. D–20761, Report No. D–20761/2400000010 (internal) Title "Treatment of DMBA–induced mammary carcinomas . . . D–20761", pp. A–15.
Proc. Natl. Acad. Sci. USA, entitled "Inhibition of growth . . . SB–75" by Korkut, et al., Vo. 88, pp. 844–848, Feb. 1991.
Amtsblatt EPA/Official Journal EPO/Journal Officiel OEB, Sep. 1993, pp. 372–378.
Zoladex in prostate cancer, A real alternative to standard endocrine therapy, pp. 1–35. (1988).
Search Report dated Aug. 1, 1994.
Article, W.Pschyrembel Klinisches Worterbuch, Berlin, 1982, pp. 231, 333, 555.

*Primary Examiner*—Jeffrey E. Russel
*Attorney, Agent, or Firm*—Cushman Darby & Cushman IP Group of Pillsbury Madison & Sutro LLP

[57] ABSTRACT

For application during the treatment of benign and malign tumour diseases, the product according to the invention containing the initial dose of Cetrorelix acetate and one or more maintenance doses of Cetrorelix acetate, Cetrorelix embonate or a slow-release form of Cetrorelix, is used as a combination preparation for treatment to be administered at specific time intervals.

25 Claims, No Drawings

PRODUCTS FOR ADMINISTERING AN INITIAL HIGH DOSE OF CETRORELIX AND PRODUCING A COMBINATION PACKAGE FOR USE WHEN TREATING DISEASES

The following substances are available for treating hormone-dependent malignant diseases; Zoladex® (INN: Goserelin) and Decapeptyl® (INN: Triptorelin). Zoladex® is injected subcutaneously in the form of a long cylinder with length 1 cm and diameter 1 mm, using a special applicator. Decapeptyl® as in the form of a microcapsule emulsion which is also applied subcutaneously. Both forms ensure continuous delivery of active substance to the surrounding tissue. The mode of action of both substances is that of a superagonist.

Cetrorelix (INN) is an antagonist for LHRH. The mode of action is completely different from that of the known superagonists. Synthesis and a few important pharmacological effects are described in EP 299 402. This indicates that different doses are required for treatment with Cetrorelix.

In clinical trials, a daily dose of 10 mg showed a complete suppression of the hormone concentration to castration level. This high daily dose cannot be applied in slow-release forms which are intended to act over a long period of time, for example several months. The depot injected under the skin would be too voluminous and would no longer be acceptable. Therefore there is the object of providing a product for reliable and acceptable application.

In the case of DMBA-induced mammary cancers in rats, it has now been found that successful treatment results from an initial high dose and a further dose which is not active when administered on its own.

This surprising observation in animals was also confirmed in humans. In trials, it was found that after injection of an initial dose of 10 mg, which led to suppression of LH, FSH and testosterone, suppression of LH, FSH and testosterone was maintained with maintenance doses of 1 mg every 12 hours, 2 mg every 24 hours and 1 mg every 24 hours. The trial was performed over three weeks. The maintenance doses applied above were not sufficient by application on their own; suppression of LH, FSH and testosterone is not achieved.

This presents a simple and reliable way of achieving the object, by providing products which contain the active substance in an initial dose with the amount 1–60 mg in a lyophilisate ampoule or several lyophilisate ampoules and which contain the maintenance dose in either one or several lyophilisate ampoules in a slow-release form with a rate of delivery of 0.1–10 mg/day for the whole period of treatment or lyophilisate ampoules which contain the amount of active substance, which is not in a slow-release form, in an amount of 0.1–10 mg.

Similar products for use during the treatment of tumour diseases with oxazaphosphorine-type alkylants, which contain the detoxifying agent Mesna and the anti-tumour agent in a combination package, are known from EP 2495. In that case, the doctor is provided with a product for reliably avoiding the urotoxic side effects of oxazophosphorine anti-tumour agents.

In this case there is a different problem. It is not a matter of providing a pharmacological product which is capable of suppressing the side effects of anti-tumour treatment, but of providing a pharmacalogical product which provides the doctor with the initial dose and the maintenance doses which are required in one package. This means that the reliability of treatment is increased, mistakes in the everyday routine of hospitals are avoided and compliance is increased.

In addition, there is the potential possibility of lowering the cost of treatment and reducing side effects, due to the smaller amount of biologically active substance used.

The initial dose is present in the product as a readily soluble salt, for example as the acetate. The acetate is produced, for example, as follows:

approximately 1.5 l of water for injection purposes are initially placed in a suitable glass vessel. 210 g of water for injection purposes are initially placed in another glass vessel and 91.17 g of acetic acid are added. The calculated amount of Cetrorelix acetate (1.62–1.695 g. depending on the concentration of the feedstock used) is dissolved with stirring in the prepared 30% strength acetic acid. This solution is transferred to the glass vessel containing 1.5 l of water for injection purposes, 82.2 g of mannitol are added, dissolved and made up to 3039 g with water for injection purposes.

On-line process checks:
pH: 2.5–3.0
Density: 1.009–1.017 g/cm$^3$ at 20° C.
Calculation index: 1.227–1.340 at 440 nm and 20° C.

The solutions are sterilised by filtration through a suitable membrane filter (pore size 0.2 μm, under aseptic conditions). The first 100 ml are discarded. The filters are sterilised with steam under pressure. Cetrorelix solution for freeze-drying is stored under protection against recontamination. The solution is immediately metered into DIN 2R injection vials which are colourless and hydrolytic class I, under aseptic conditions, and provided with sterile freeze-drying stoppers. The nominal amount is 2.0 ml=2.026 g.

The 2 ml injection vials were first rinsed on an injection phial washing machine and dried and sterilised with hot air. The cleansed freeze-drying stoppers were autoclaved. The pre-sealed injection vials were transferred to a freeze-drying unit and lyophilised at a shelf temperature of −40° C. rising to +20° C. Then the unit was flooded with sterile nitrogen, the vials were sealed in the unit and the stoppers were made secure with flared-fitting lids.

The injection vials are visually inspected for faulty seals and external defects. Faulty injection vials are removed and destroyed.

Cetrorelix lyophilisate 1 mg is a white, solid freeze-dried cake in a colourless 2 ml injection phial which is sealed with grey freeze-drying stoppers and yellow flip-off flared-fitting lids.

The maintenance dose can also be formulated as the acetate, as the embonate or embedded in microparticles in accordance with DE-OS 42 23 282.1 or E. Korkut, L. Bokser, A. M. Comaru-Schally, K. Groot and A. V. Schally; Inhibition of growth of experimental prostate cancer with sustained delivery systems (microcapsules and microgranules) of the luteinizing hormone-releasing hormone antagonist SB-75, Proc. Natl. Acad. Sci. USA, vol. 88, pp. 844–848 (1991).

The embonate, for example, is prepared as follows:

An aqueous solution of embonic acid containing excess alkali is combined with the acetic acid Cetrorelix acetate solution at an equimolar ratio of peptide (calculated as free base) to embonic acid, wherein the embonic acid precipitates as yellow particles. On adding dilute caustic soda solution until the pH is 7–7.5, the embonic acid dissolves and precipitates with the decapaptide as a white Cetrorelix embonate salt with the molar composition peptide:embonic acid of e.g. 2:1 (mol/mol). The precipitate is filtered off, washed with $H_2O$ and dried.

The initial dose and the maintenance dose are packed together in a single package so that an adequate amount of substance is provided for one week or one month of treatment.

A one month treatment pack, for example, is made up as follows:

A container or several containers are filled with the initial dose of Cetrorelix acetate lyophilisate. The amount used is between 1 mg and 60 mg of lyophilisate per container.

Up to 30 further containers are filled with the maintenance dose of Cetrorelix acetate lyophilisate. The amount used is between 0.1 and 30 mg per container.

The maintenance dose may also be presented as a slow-release formulation.

We claim:

1. A kit comprising
   (a) an initial dose of an LHRH antagonist suitable for treatment of hormone-dependent conditions, and
   (b) at least one maintenance dose of the LHRH antagonist, in an amount which is insufficient for treating the hormone-dependent conditions when administered alone.

2. The kit of claim 1, wherein the LHRH antagonist of (b) is in a slow-releasing formulation.

3. The kit of claim 1, wherein the LHRH antagonist is Cetrorelix.

4. The kit of claim 3, wherein the initial dose of Cetrorelix is between about 1 and about 60 mg.

5. The kit of claim 3, wherein the maintenance dose of Cetrorelix is between about 0.1 and about 60 mg.

6. The kit of claim 3, wherein the maintenance dose of Cetrorelix consists of a slow-releasing formulation.

7. A method of treating a hormone-dependent condition which comprises the steps of
   (a) administering an initial dose of an LHRH antagonist to a person having a hormone-dependent condition, and
   (b) then administering to that person a maintenance dose of an LHRH antagonist in an amount which is insufficient for treating the hormone-dependent conditions when administered alone.

8. The method of claim 7, wherein the maintenance dose of the LHRH antagonist is a slow-releasing formulation.

9. The method of claim 7, wherein the LHRH antagonist is Cetrorelix.

10. The method of claim 7, wherein Cetrorelix of the maintenance dose consists of a slow-releasing formulation.

11. The method of claim 9, wherein the initial dose of Cetrorelix is between about 1 and about 60 mg, and the maintenance dose of Cetrorelix is between about 0.1 and about 30 mg.

12. The method of claim 11, wherein the Cetrorelix of the maintenance dose consists of a slow-releasing formulation.

13. The method of claim 7, wherein the hormone-dependent condition is prostate cancer.

14. The method of claim 7, wherein the hormone-dependent condition is endometrial hyperplasia.

15. The method of claim 7, wherein the hormone-dependent condition is benign prostate hypertrophy.

16. The method of claim 7, wherein the hormone-dependent condition is mammary carcinoma.

17. The method of claim 7, wherein the hormone-dependent condition is ovarian carcinoma.

18. The method of claim 7, wherein the hormone-dependent condition is uterine fibroma.

19. The method of claim 7, wherein the hormone-dependent condition is pubertas praecox.

20. The method of claim 7, wherein the hormone-dependent condition is pituitary adenomas.

21. A method for decreasing male fertility comprising the steps of
   (a) administering to a male an initial dose of an LHRH antagonist, and
   (b) then administering to that male a maintenance dose of an LHRH antagonist in an amount which is insufficient for decreasing male fertility when administered alone.

22. The method of claim 21, wherein the LHRH antagonist is Cetrorelix.

23. The method of claim 21, wherein the Cetrorelix of the maintenance dose consists of a slow-releasing formulation.

24. The method of claim 22, wherein the initial dose of Cetrorelix is between about 1 and 60 mg, and the maintenance dose of Cetrorelix is between about 0.1 and 30 mg.

25. The method of claim 24, wherein the Cetrorelix of the maintenance dose comprises Cetrorelix pamoate or Cetrorelix acetate in a slow-releasing form.

\* \* \* \* \*